United States Patent [19]

Young

[11] Patent Number: 4,567,268

[45] Date of Patent: Jan. 28, 1986

[54] PROCESS FOR PREPARATION OF CERTAIN TETRAHYDROFURO[3,4-B]PYRIDINES

[75] Inventor: Steven D. Young, Lansdale, Pa.

[73] Assignee: Merck & Co., Inc., Rahway, N.J.

[21] Appl. No.: 596,333

[22] Filed: Apr. 3, 1984

[51] Int. Cl.$^4$ .......................................... C07D 491/048
[52] U.S. Cl. .................................................... 546/116
[58] Field of Search ........................................ 546/116

[56] References Cited

U.S. PATENT DOCUMENTS 4,284,634  8/1981  Sato ...................................... 546/116

FOREIGN PATENT DOCUMENTS 2105989  4/1983  United Kingdom .

OTHER PUBLICATIONS

Perronnet et al., Chem. Abstracts, vol. 82, 155398c, (1975).
Fierer et al., Reagents for Organic Synthesis vol. 1, Wiley, pp. 967–970, (1967).
Meyer et al., Arzneim–Forsch/Drug Research 33 (I), Nrl (1983).
Zigeuner et al., Monatschefte fur Chemie, 97, 1408, (1966).

Primary Examiner—Henry R. Jiles
Assistant Examiner—Bernard I. Dentz
Attorney, Agent, or Firm—Alice O. Robertson; Joseph F. DiPrima; Michael C. Sudol, Jr.

[57] ABSTRACT

A facile process for the preparation of certain tetrahydrofuro[3,4-b]pyridines is described. The compounds have pharmacological properties useful in the study and treatment of cardiovascular diseases.

6 Claims, No Drawings

PROCESS FOR PREPARATION OF CERTAIN TETRAHYDROFURO[3,4-B]PYRIDINES

This invention is directed to a process for the preparation of certain tetrahydrofuro[3,4-b]-pyridines.

BACKGROUND OF THE INVENTION

Recently it has been reported that 1,4,5,7-tetrahydrofuro[3,4-b]pyridine compounds which may be represented by the formula

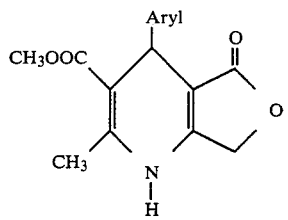

have physiological properties which are antithetical to those possessed by

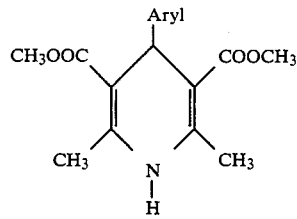

which have been studied extensively as calcium slow channel blocking drugs. GB Pat. No. 2,105,989A, U.S. Pat. No. 4,284,634 and H. Meyer et al, Arzneim-Forsch/Drug Research 33(I) Nr 1 (1983), p. 106 teach various dihydropyridines including the foregoing 1,4,5,7-tetrahydrofuro[3,4-b]pyridine compounds to have useful properties of increasing the influx of calcium ion into cells and to be adaptable for use in combating coronary and vascular diseases. The 1,4,5,7-tetrahydrofuro[3,4-b]pyridine compounds have been prepared by condensing a protected 4-hydroxyacetoacetic ester with methyl β-aminocrotonate and an appropriate aldehyde and the resulting dihydropyridine compound heated with alkali to remove the protecting group and to effect cyclization. The process is cumbersome, especially since the 4-hydroxyacetoacetic ester is not readily available and the preparation of the protected 4-hydroxyacetoacetic ester is a multistep procedure. It is desirable to provide for a facile synthesis of 1,4,5,7-tetrahydrofuro[3,4-b]pyridine compounds for studies directed to mechanism of drug action and for ultimate development of superior agents for the treatment of cardiovascular diseases.

Although bromine has been reported to react with 5-carbethoxy-6-methyldihydropyrimidine-2-one to form a bromomethyl compound which could be caused to cyclize on heating with phenol or aqueous ethanol, G. Zigeuner et al., Monatshefte fur Chemie, 97, 1408 (1966), no useful bromomethyl compound was obtained by reacting bromine with the non-analogous dihydropyridine compounds and 1,4,5,7-tetrahydrofuro[3,4-b]-pyridine compounds could not be satisfactorily produced. Thus, a good synthetic method, particularly from readily available starting materials is highly desirable.

DESCRIPTION OF THE INVENTION

According to the present invention there has been discovered a simple single step process for preparing a 1,4,5,7-tetrahydrofuro[3,4-b]pyridine compound represented by the formula

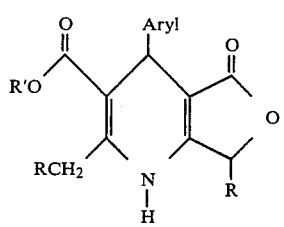

in good yields and in high purity by reacting a 1,4-dihydropyridine diester compound represented by the formula

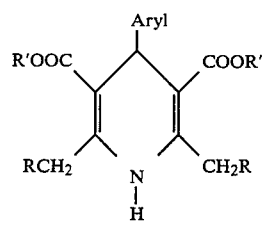

with a bromine generating agent wherein aryl embraces monocyclic, polycyclic including condensed polycyclic, and heterocyclic aromatic radicals which additionally may be substituted, and R is hydrogen or alkyl and R' is a residue of a hydroxy compound (alcohols and phenols) capable of forming esters with a carboxyl group. By a "single-step" process is meant that between the placement of the reactants in the reaction vessel and recovery of product therefrom, no manipulative procedures for isolation of intermediates is necessary.

The process is useful for the preparation of 2-alkyl-4aryl-5-oxo-1,4,5,7-tetrahydrofuro[3,4-b]-pyridine-3-carboxylate compounds which have been found to have positive inotropic effects and therefore useful as a pharmacological tool for investigating calcium channel blocking agents and which as reported in the art are useful as cardiovascular agents. These and analogous 1,4,5,7-tetrahydrofuro[3,4-b]-pyridine compounds for which the process of the present invention is especially directed are those in which the aryl in Formula I is a substituted phenyl group, particularly those which may be represented by Formula IA.

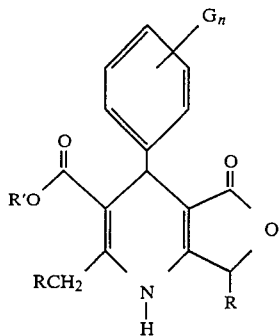

IA

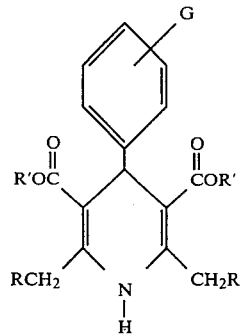

IIA

In this and succeeding formulas, R is hydrogen or methyl, R' is alkyl, hydroxyalkyl, alkoxyalkyl, haloalkyl, aralkyl, cyanoalkyl, nitroalkyl, phenyl, alkylphenyl, alkoxyphenyl, halophenyl and nitrophenyl; and G is alkyl, alkoxy, alkoxyalkyl, alkylenedioxy, mono- and polyhaloalkyloxy, alkylaminoalkyl, halo, trifluoromethyl, cyano, nitro, acyl, aryl, aralkyloxy, aryloxy, carbalkoxy, alkylsulfonyl, arylsulfonyl, alkylsulfinyl and arylsulfinyl; n is from 0 to 5. Where the expression "alkyl" or "alkoxy" is employed in each instance it is intended to embrace lower alkyl or alkoxy from 1 to 6 carbon atoms.

Representative of substituted phenyl groups which may be present in the compounds prepared by the process of the present invention include 2-nitrophenyl, 2,4,6-trichlorophenyl, 2,3,4,5-tetramethylphenyl, 2-trifluoromethylphenyl, 3-methoxyphenyl, 3-iodophenyl, 2-methylphenyl, 3-trifluoromethylphenyl, 2-chlorophenyl, 2-trifluoromethoxyphenyl, 4-ethoxycarbonylphenyl, 3-ethoxyphenyl, 2-cyanophenyl, 2,3-dichlorophenyl, 5-chloro-2-nitrophenyl, 2-chloro-4-nitrophenyl, 2,3,4,5,6-pentafluorophenyl, 2-chloro-6-fluorophenyl, 3-benzyloxyphenyl, 2-(4-methylbenzyloxy)phenyl, 2-(4-chlorobenzyloxy)phenyl, 2-(2,6-dichlorobenzyloxy)phenyl, 2-(3,4-dichlorophenyloxy)phenyl, 2-[3-nitrobenzyloxy)phenyl], 2-(3-fluorobenzyloxy)phenyl, 2-(3-trifluoromethylbenzyloxy)phenyl, 4-ethoxymethylphenyl, 4-hydroxymethylphenyl, 2-(4-fluorobenzyloxy)phenyl, 2-(3,5-dimethylbenzyloxy)phenyl, 2-(4-chlorobenzyl)phenyl, 3-propoxyphenyl, 2-phenethyloxyphenyl, 4-biphenylyl, 4-cyanophenyl, 4-(isopropoxyethyl)phenyl and 4-acetylphenyl. Still others include 2-benzylsulfonylphenyl, 3-phenylpropylsulfinylphenyl, 2-phenylyl, 2-methoxycarbonylphenyl, ethylsulfonylphenyl, phenylsulfonylphenyl and the like.

A preferred embodiment of the process of the present invention comprises intimately contacting a 1,4-dihydropyridine diester compound having the formula with a molecular bromine generating agent in an inert dispersion medium and warming the resulting mixture to obtain the desired tetrahydrofuro[3,4-b]pyridine compound of Formula IA.

Many of the 1,4-dihydropyridine diester compounds represented by Formula IIA are readily available known drugs or drug analogs. Thus, for the preparation of tetrahydrofuro[3,4-b]pyridine corresponding to the known drugs, the invention provides a simple, single step method for their preparation. When other analogous compounds are desired the 1,4-dihydropyridine diester starting materials are easily prepared from readily obtainable starting materials by established procedures as subsequently described.

Although some product may be obtained using any bromine generating agent, not all are equally useful. Moreover, liquid bromine itself is not useful, giving a multitude of brominated products. One agent, particularly preferred, for producing good yields of the desired product in shorter reaction time, in substantially pure form or readily purifiable form is pyridinium bromide perbromide. Another suitable reagent, although less preferred is N-bromosuccinimide.

The amount of bromine generating agent with respect to the dihydropyridine diester compound may vary from substantially equimolar to about a molar excess, preferably a 20 mole percent excess, i.e., the preferred ratio of dihydropyridine diester compound to bromine generating agent is about 1:1.2.

When the bromine generating agent is pyridinium bromide perbromide, it has been found that the reaction is facilitated by the addition of an excess of pyridine.

An inert solvent is employed as a reaction or dispersion medium. The solvent acts as a solvent for the 1,4-dihydropyridine compound and as a dispersion medium for the bromine generating agent. Suitable solvents are preferably halogenated hydrocarbons such as chloroform, carbon tetrachloride, methylene bromide, methylene chloride and the like. It is essential that the solvent be dry and free of polar solvents such as ethanol. Solvents may be appropriately purified and/or dried by conventional procedures such as distilling from phosphorus pentoxide.

The reaction is carried out in a dry, inert atmosphere. This is accomplished by protecting the reaction vessel from atmospheric moisture such as with a calcium chloride drying tube or equivalent, and by providing for an atmosphere of nitrogen or argon. Since the bromine generating agent is generally insoluble in the solvent media, provision for stirring or other mixing is provided. The temperature for the reaction is in the range of from about $-5°$ C. to $100°$ C. Usually, the reactants are brought together under cooling conditions and the reaction completed at the reflux temperature of the solution. The time for reaction may be from about one hour to several hours. The actual time which is sufficient to complete the reaction may be easily determined by thin layer chromatographic (TLC) analysis.

The reaction is generally carried out by mixing together the appropriate 1,4-dihydropyridine diester compound of Formula II or IIA and a bromine generating agent in an inert solvent or dispersion medium in a dry inert atmosphere in the temperature range of from about −5° C. to ambient temperature, then heating the mixture to reflux temperature and maintaining the mixture at this temperature for time sufficient to complete the reaction with the formation of the desired tetrahydrofuro[3,4-b]-pyridine compound of Formula I or IA.

When employing pyridine hydrobromide perbromide as bromine generating agent, the reaction is carried out preferably by adding the agent in one portion to dry solution of the dihydropyridine diester compound of Formula II or IIA in an inert solvent containing pyridine maintained in a dry, inert atmosphere at a temperature in the range of from about −5° to +5° C., preferably about 0° C., stirring the resulting mixture for from about 15 to about 45 minutes, preferably about 30 minutes, and thereafter heating to reflux temperature of the solution and maintaining at this temperature until substantial completion of the reaction with the formation of the desired product of Formula I or IA in the reaction mixture. The product may be removed from the reaction mixture by diluting with reaction solvent, washing and resulting solution successively with dilute acid and brine, thereafter drying and evaporating the solvent under reduced pressure to obtain the product as residue. The product may be purified by conventional procedures, preferably by chromatographing on silica gel employing 65% ethyl acetate-35% hexane as eluant. By this process, substantially pure, white crysytalline product is obtained in good yields.

The following examples illustrate the invention but are not to be construed as limiting:

EXAMPLE I

Methyl 2-methyl-4-phenyl-5-oxo-1,4,5,7-tetrahydrofuro[3,4-b]pyridine-3-carboxylate

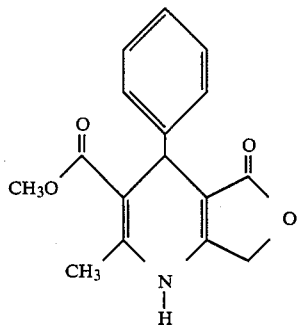

1.58 grams of 80 percent pyridinium bromide perbromide (3.95 millimoles) was added in one portion to a cooled to 0° C. solution of 1.00 gram (3.32 millimoles) of dimethyl 2,6-dimethyl-4-phenyl-1,4-dihydropyridine-3,5-dicarboxylate and 0.4 milliliter of pyridine in 20 milliliters of dry ethanol-free chloroform. The resulting mixture was stirred for 45 minutes at 0° C. and then heated at reflux temperature for 1.3 hous. Thereafter, the mixture was cooled to room temperature, diluted with chloroform and the resulting solution washed successively with 2N hydrochloric acid and brine, dried over magnesium sulfate, and dried solution filtered to remove the drying agent, and then subjected to reduce pressure to vaporize the solvent and to recover as residue 1.41 grams of product as a yellow oil. The oil was chromatographed on silica gel using 70 percent ethyl acetate—30 percent hexane as eluant to obtain 595 milligrams (63 percent yield) of purified methyl 2-methyl-4-phenyl-5-oxo-1,4,5,7-tetrahydrofuro[3,4-b]-pyridine-3-carboxylate product which after recrystallization from ethyl acetate-hexane and drying at 60° C. at 0.005 millimeters mercury pressure for 17 hours had a melting point of 193°–196° C. Elemental analyses for the product were as follows:

Calcd. for $C_{16}H_{15}NO_4$ (m.w. 285.3): C, 67.36; H, 5.30; N, 4.91. Found: C, 67.74; H, 5.33; N, 4.80.

EXAMPLE II

Methyl 2-methyl-4-(o-tolyl)-5-oxo-1,4,5,7-tetrahydrofuro[3,4-b]pyridine-3-carboxylate In an operation carried out in a manner similar to that described in the preceding example, 1.52 grams of 80 percent pyridinium bromide perbromide (3.81 millimoles) was added in one portion to a solution of 1.00 gram (3.17 millimoles) of dimethyl 2,6-dimethyl-4-(o-tolyl)-1,4-dihydropyridine-3,5-dicarboxylate and 0.40 milliliter of pyridine in 20 milliliters of dry chloroform cooled to 0° C. The mixture was stirred for 30 minutes at 0° C., then at reflux temperature for 1.5 hours. Thereafter, the mixture was cooled, washed successively with hydrochloric acid and brine, dried, subjected to reduced pressure to remove the solvent and to obtain as residue crude methyl 2-methyl-4-(o-tolyl)-5-oxo-1,4,5,7-tetrahydrofuro[3,4-b]pyridine-3-carboxylate product. The crude product was chromatographed on silica and eluted with 65 percent ethyl acetate—35 percent hexane to obtain 0.58 gram (61 percent yield) of white crystalline material which after recrystallizing from ethyl acetate-hexane and drying at 80° C./0.005 mm Hg for 17 hours had a melting point of 224°–225° C. and the following analyses:

Calcd for $C_{17}H_{17}NO_4$ (m.w. 299.3): C, 68.22; H, 5.72; N, 4.68. Found: C, 68.04; H, 5.70; N, 4.61.

EXAMPLE III

Methyl 2-methyl-4-(3,4-methylenedioxyphenyl)5-oxo-1,4,5,7-tetrahydrofuro[3,4-b]pyridine-3-carboxylate

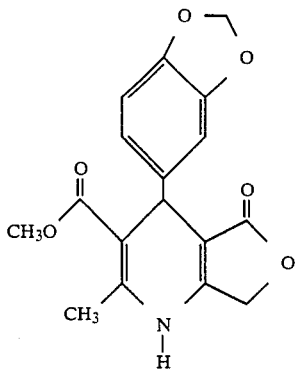

In a similar manner, 2.78 grams (6.95 millimoles) of pyridinium bromide perbromide was added in one portion to a cooled to 0° C. mixture of 2 grams of dimethyl 2,6-dimethyl-4-(3,4-methylenedioxyphenyl)-1,4-dihydropyridine-3,5-dicarboxylate and 0.81 milliliter of pyridine in 40 milliliters of ethanol-free chloroform, the resulting mixture stirred at 0° C. for 30 minutes then heated at reflux temperature for 90 minutes to obtain a methyl 2-methyl-4-(3,4-methylenedioxyphenyl)-5-oxo-1,4,5,7-tetrahydrofuro[3,4-b]pyridine-3-carboxylate product in the reaction mixture. The product was recovered in a manner similar to that previously described and purified over silica with 70/30 ethyl acetate/hexane to obtain 740 milligrams (39 percent yield) of white crystals. An analytical sample having a melting point of 226°–228° C. was obtained by recrystallizing from ethyl acetate/hexane and drying at 80° C./0.005 millimeters Hg pressure for 48 hours. Elemental analyses were as follow:

Calcd for $C_{17}H_{15}NO_6$ (m.w. 329.3): C, 62.00; H, 4.59; N, 4.25. Found: C, 61.85; H, 4.51; N, 4.28.

EXAMPLE IV

Methyl 2-methyl-4-(3-bromophenyl)-5-oxo-1,4,5,7-tetrahydrofuro[3,4-b]pyridine-3-carboxylate In a similar manner, 2.02 grams (2.52 grams of 80 percent; 6.31 millimoles) of pyridinium bromide perbromide was added in a single portion to a solution of 2 grams (5.26 millimoles) of dimethyl 2,6-dimethyl-4-(3-bromophenyl)-1,4-dihydropyridine-3,5-dicarboxylate and 0.79 gram (10.0 millimoles) of pyridine in 40 milliliters of chloroform (distilled from $P_2O_5$) which had been cooled to 0° C. The resulting mixture was stirred at this temperature for 30 minutes and then heated at reflux temperature for 1.5 hours. Thereafter, the mixture was allowed to cool to room temperature and diluted with chloroform; the diluted solution washed with 2N hydrochloric acid and brine, dried, and the solvent evaporated to obtain methyl 2-methyl-4-(3-bromophenyl)-5-oxo-1,4,5,7-tetrahydrofuro[3,4-b]pyridine-3-carboxylate product as a yellow foamy material. The latter was chromatographed on silica gel employing 60 percent ethyl acetate—40 percent hexane as eluant to obtain 790 milligrams (41 percent yield) of purified methyl 2-methyl-4-(3-bromophenyl)-5-oxo-1,4,5,7-tetrahydrofuro[3,4-b]pyridine-3-carboxylate product as a white crystalline solid. An analytical sample of m.p. 229°–231° C. was prepared by recrystallizing from ethyl acetate-hexane. Elemental analyses were as follows:

Calcd for $C_{16}H_{14}BrNO_4$ (m.w. 364.2): C, 52.77; H, 3.87; N, 3.85. Found: C, 52.91; H, 3.92; N. 4.04.

EXAMPLE V

Methyl 2-methyl-4-(2-nitrophenyl)-5-oxo-1,4,5,7-tetrahydrofuro[3,4-b]pyridine-3-carboxylate In a similar manner, 2.77 grams of 80 percent pyridinium bromide perbromide (6.93 millimoles) was added in one portion to a cooled to 0° C. solution of 2.00 grams (5.77 millimoles) of dimethyl 2,6-dimethyl-4-(2-nitrophenyl)-1,4-dihydropyridine-3,5-dicarboxylate (nifedipine), and 0.81 milliliter of pyridine in 40 milliliters of chloroform. The resulting mixture was stirred at 0° C. for 30 minutes, at reflux temperature for 90 minutes, allowed to cool to room temperature, diluted with chloroform, washed with 2N hydrochloric acid and with brine, dried, and the solvent vaporized in vacuo to obtain a crude product residue. The latter was flash chromatographed (J. Org. Chem. 43, 2923 (1978)) on silica gel employing 70 percent ethyl acetate—30 percent hexane as eluant to obtain 0.45 gram (24 percent yield) of purified methyl 2-methyl-4-(2-nitrophenyl)-5-oxo-1,4,5,7-tetrahydrofuro-[3,4-b]-pyridine-3-carboxylate product which after recrystallizing from ethyl acetate hexane had a melting point of 261°–263° C. (dec.). Elemental analyses were as follows:

Calcd for $C_{16}H_{14}N_2O_6$ (m.w. 330.3); C, 58.18; H, 4.27; N, 8.40. Found: C, 58.41; H, 4.27; N, 8.23.

EXAMPLE VI

Methyl 2-methyl-4-(2-trifluoromethylphenyl)-5-oxo-1,4,5,7-tetrahydrofuro[3,4-b]pyridine-3-carboxylate In a manner similar to that described in the preceding examples, 2.60 grams of 80 percent pyridinium bromide perbromide was added to a cooled to 0° C. solution of 2.00 grams (5.42 millimole) of dimethyl 2,6-dimethyl-4-(2-trifluoromethylphenyl)-1,4-dihydropyridine-3,5-dicarboxylate and 0.81 milliliter of pyridine in 40 milliliters of chloroform. The resulting mixture was stirred one-half hour at 0° C. and 90 minutes under reflux, then allowed to cool to room temperature, diluted with chloroform, washed with 2N hydrochloric acid and brine, dried, the solvent evaporated in vacuo to obtain a crude product. The product was purified by chromatographing on silica gel with 70 percent ethyl acetate—30 percent hexane as eluant to obtain 1.08 grams (56 percent yield) of white crystals of a methyl 2-methyl-4-(2-trifluoromethylphenyl)-5-oxo-1,4,5,7-tetrahydrofuro[3,4-b]pyridine-3-carboxylate product which after recrystallization from ethyl acetate-hexane had a melting point of 239°–241° C. Elemental analyses were as follows:

Calcd for $C_{17}H_{14}F_3NO_4$ (m.w. 353.3): C, 57.79; H, 3.99; N, 3.96. Found: C, 57.99; H, 3.94; N, 3.78.

EXAMPLE VII

Methyl 2-methyl-4-(2-methoxyphenyl)-5-oxo-1,4,5,7-tetrahydrofuro[3,4-b]pyridine-3-carboxylate In a manner similar to that described in the preceding examples, 1.45 grams of 80 percent pyridinium bromide perbromide was added to a cooled to 0° C. solution of 1.00 gram (3.02 millimoles) of dimethyl 2,6-dimethyl-4(2-methoxyphenyl)-1,4-dihydropyridine-3,5-dicarboxylate and 0.40 milliliter of pyridine in 20 milliliters of chloroform. The mixture was then stirred at 0° C. for about 30 minutes and at reflux temperature for about 90 minutes. Thereafter the mixture was allowed to cool, diluted with chloroform, washed with 2N hydrochloric acid and brine, dried and the solvent evaporated to obtain a crude product residue. The latter was flash chromatographed on 35 grams of silica gel to obtain 510 milligrams (54 percent yield) of purified methyl 2-methyl-4-(2-methoxyphenyl)-5-oxo-1,4,5,7-tetrahydrofuro[3,4-b]pyridine-3-carboxylate product. A portion of the product was recrystallized from ethyl acetate-hexane for elemental analyses which were as follows:

Calcd for $C_{17}H_{17}NO_5$ (m.w. 315.3): C, 64.75; H, 5.43; N. 4.44. Found: C, 64.91; H, 5.43; N, 4.46.

The product had a melting point of 212°–215° C., which was the same as that when prepared employing N-bromosuccinimide.

EXAMPLE VIII

Methyl 2-methyl-4-(2,3,4,5,6-pentafluorophenyl)-5-oxo-1,4,5,7-tetrahydrofuro[3,4-b]pyridine-3-carboxylate 2.00 grams (5.11 millimoles) of dimethyl 2,6-dimethyl-4-(2,3,4,5,6-pentafluorophenyl)-1,4-dihydropyridine-3,5-carboxylate, 1.36 grams (7.67 millimoles) of N-bromosuccinimide and 40 milliliters of carbon tetrachloride were mixed together in an atmosphere of nitrogen and heated at reflux temperature for three hours with vigorous stirring. The mixture was allowed to cool to room temperature, then diluted with 200 milliliters of chloroform, washed with water and brine, dried over magnesium sulfate. The drying agent was filtered and the solvent evaporated in vacuo to obtain a yellow oil which was chromatographed on silica with 55 percent ethyl acetate—45 percent hexane to obtain a methyl 2-methyl-4-(2,3,4,5,6-pentafluorophenyl)-5-oxo-1,4,5,7-tetrahydrofuro[3,4-b]pyridine-3-carboxylate product as a white solid. The solid was recrystallized from ethyl acetate hexane to obtain as first crop, 309 milligrams of purified crystalline product of m.p. 269°–271° C. Elemental analyses were as follows:

Calcd for $C_{16}H_{10}NO_4F_5$ (m.w. 375.2): C, 51.21; H, 2.69; N, 3.73. Found: C, 51.28; H, 2.63; N, 3.55.

EXAMPLE IX

In operations carried out in a manner similar to that described in Example VIII, the following compounds were prepared:

Methyl 2-methyl-4-phenyl-5-oxo-1,4,5,7-tetrahydrofuro[3,4-b]pyridine-3-carboxylate 0.1/8 ethyl acetate (solvate), m.p. 205°–208° C. mixing in argon atmosphere and by heating at reflux temperature for about 2.5 hours, 2.00 grams (6.64 millimoles) of dimethyl 2,6-dimethyl-4-phenyl-pyridine-3,5-dicarboxylate and 1.77 grams (9.96 millimoles) of N-bromosuccinimide in 40 milliliters of carbon tetrachloride.

Methyl 2-methyl-4-(2-methoxyphenyl)-5-oxo-1,4,5,7-tetrahydrofuro[3,4-b]pyridine-3-carboxylate, m.p. 212°–215° C., mixing together in argon atmosphere, then heating at reflux temperature for about 3 hours, 2.00 grams (6.04 millimoles) of dimethyl 2,6-dimethyl-4-(2-methoxyphenyl)-1,4-dihydropyridine-3,5-dicarboxylate and 1.61 grams (9.05 millimoles) of N-bromosuccinimide in 40 milliliters of carbon tetrachloride.

Methyl 2-methyl-4-(2-trifluoromethylphenyl)-5-oxo-1,4,5,7-tetrahydrofuro[3,4-b]pyridine-3-carboxylate, m.p. 225°–229° C. by mixing together in argon atmosphere and heating at reflux temperature for about 3 hours, 2.00 grams (5.42 millimoles) of dimethyl 2,6-dimethyl-4-(2-trifluoromethylphenyl)-1,4-dihydropyridine-3,5-dicarboxylate and 1.45 grams (8.12 millimoles) of N-bromosuccinimide in 40 milliliters of carbon tetrachloride.

Methyl 2-methyl-4-(3,4-methylenedioxyphenyl)-5-oxo-1,4,5,7-tetrahydrofuro[3,4-b]pyridine-3-carboxylate by heating together 3.00 grams (8.69 millimoles) of dimethyl 2,6-dimethyl-4-(3,4-methylenedioxyphenyl)-1,4-dihydropyridine-3,5-dicarboxylate and 2.32 grams (13.03 millimoles) of N-bromosuccinimide in 50 milliliters of carbon tetrachloride.

Methyl 2-methyl-4-(o-tolyl)-5-oxo-1,4,5,7-tetrahydrofuro[3,4b]pyridinecarboxylate m.p. 221°–222° C., by heating together 2.79 grams (8.85 millimoles) of dimethyl 2,6-dimethyl-4-(o-tolyl)-1,4-dihydropyridine-3,5-dicarboxylate and 2.36 grams (13.27 millimoles) of N-bromosuccinimide in 50 milliliters of carbon tetrachloride.

EXAMPLE X

In an operation carried out in a manner similar to those described in Examples I–VII, methyl 2-methyl-4-(2,3,4,5,6-pentafluorophenyl)-5-oxo-1,4,5,7-tetrahydrofuro[3,4-b]pyridine-3-carboxylate, m.p. 269°–217° C., was prepared by adding 2.45 grams of 80 percent pyridinium bromide perbromide (6.13 millimoles to a cooled solution of 2.00 grams (5.11 millimoles) of dimethyl 2.6-dimethyl-4-(2,3,4,5,6-pentafluorophenyl)-1,4-dihydropyridine-3,5-dicarboxylate and 0.81 milliliter (10.1 millimoles) of pyridine in 40 milliliters of chloroform, then heating the mixture under reflux and thereafter diluting, washing, drying, vaporizing the solvent and purifiying by chromatographing on silica gel with 60 percent ethyl acetate—40 percent hexane as eluant. The yield of the purified product was 680 milligrams (35 percent).

EXAMPLE XI

Methyl 2-ethyl-4-(4-chlorophenyl)-5-oxo-7-methyl-1,4,5,7-tetrahydrofuro[3,4-b]pyridine-3-carboxylate

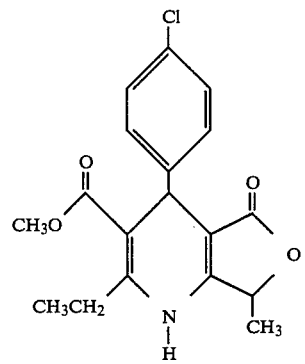

In a similar manner 2.02 grams (2.52 grams of 80 percent; 6.31 millimoles) of pyridinium bromide perbromide is added in a single portion to a cooled to 0° C.

solution of 1.91 grams (5.26 millimoles) of dimethyl 2,6-diethyl-4-(4-chlorophenyl)-1,4-dihydropyridine-3,5-dicarboxylate and 0.79 gram (10.1 millimoles) of pyridine in 40 milliliters of chloroform. The resulting mixture is stirred at this temperature for 30 minutes, then at reflux temperature for 90 minutes. The mixture is then allowed to cool, diluted with chloroform, the diluted solution washed with 2N hydrochloric acid and brine, and dried; the solvent then is evaporated to obtain the methyl 2-ethyl-4-(4-chlorphenyl)-5-oxo-7-methyl-1,4,5,7-tetrahydrofuro[3,4-b]pyridine 3-carboxylate product as residue. The residue is purified by chromatographing on silica gel using ethyl acetate-hexane as eluant.

EXAMPLE XII

In operations employing pyridinium bromide perbromide as brominating agent and carried out in a manner similar to that described in Examples I–VII, the following compounds may be prepared:

Methyl 2-methyl-4-(3-t-butylphenyl)-5-oxo-1,4,5,7-tetrahydrofuro[3,4-b]pyridine-3-carboxylate from dimethyl 2,6-dimethyl-4-(3-t-butylphenyl)-1,4-dihydropyridine-3,5-dicarboxylate.

Methyl 2-methyl-4-(3,5-dimethylphenyl)-5-oxo-1,4,5,7-tetrahydrofuro[3,4b]pyridine-3-carboxylate from dimethyl 2,6-dimethyl-4-(3,5-dimethylphenyl)-1,4-dihydropyridine-3,5-dicarboxylate.

Methyl 2-ethyl-4-(3,5-dimethylphenyl)-5-oxo-7-methyl-1,4,5,7-tetrahydrofuro[3,4-b]pyridine-3-carboxylate from dimethyl 2,6-diethyl-4-(3,5-dimethylphenyl)-1,4-dihydropyridine-3,5-dicarboxylate.

Methyl 2-methyl-4-(4-cyanophenyl)-5-oxo-1,4,5,7-tetrahydrofuro[3,4-b]pyridine-3-carboxylate from dimethyl 2,6-methyl-4-(4-cyanophenyl)-1,4-dihydropyridine-3,5-dicarboxylate.

Methyl 2-ethyl-4-(4-$\alpha,\alpha,\alpha$-trifluoroacetylphenyl)-5-oxo-7-methyl-1,4,5,7-tetrahydrofuro[3,4-b]-pyridine-3-carboxylate from dimethyl 2,6-diethyl-4-(4-$\alpha,\alpha,\alpha$-trifluoroacetylphenyl)-1,4-dihydropyridine-3,5-dicarboxylate.

Methyl 2-methyl-4-(4-dimethylaminomethylphenyl)-5-oxo-1,4,5,7-tetrahydrofuro[3,4-b]pyridine-3-carboxylate from dimethyl 2,6-dimethyl-4-(4-dimethylaminomethylphenyl)-1,4-dihydropyridine-3,5-dicarboxylate.

EXAMPLE XIII t-Butyl 2-methyl-4-phenyl-5-oxo-1,4,5,7-tetrahydrofuro[3,4-b]pyridine-3-carboxylate In a manner similar to that previously described, 1.14 gram of 80 percent pyridinium bromide perbromide (2.85 millimoles) was added to a cooled to 0° C. solution of 1.00 gram (2.59 millimoles) of di-t-butyl 2,6-dimethyl-4-phenyl-1,4-dihydropyridine-3,5-dicarboxylate and 0.81 milliliter of pyridine in 20 milliliters of dry chloroform. The resulting mixture was stirred for 30 minutes at 0° C. and then heated at reflux for 90 minutes. Thereafter, the mixture was cooled to room temperature, diluted with 200 milliliters of ethyl acetate and washed successively with 5 percent hydrochloric acid and brine, dried over magnesium sulfate, then filtered to remove the drying agent and the filtrate subjected to reduced pressure to vaporize the solvent and recover 0.90 gram of product as a yellow oil. The oil was chromatographed on 50 grams of silica gel using 1:1 ethyl acetate-hexane as eluant to obtain 250 milligrams (29 percent yield) of white crystalline t-butyl 2-methyl-4-phenyl-5-oxo-1,4,5,7-tetrahydrofuro[3,4-b]pyridine-3-carboxylate product which after recrystallization from diethyl ether and drying at 70° C./0.05 millimeters Hg pressure for 48 hours and 100° C./0.005 millimeters Hg for 24 hours had a melting point of 185°–188° C. Elemental analyses for the product were as follows:

Calc'd for $C_{19}H_{21}NO_4$ (m.w. 327.4): C, 69.71; H, 6.47; N, 4.28. Found: C, 69.34; H, 6.55; N, 4.65.

EXAMPLE XIV

2-Hydroxyethyl 2-methyl-4-phenyl-5-oxo-1,4,5,7-tetrahydrofuro[3,4-b]pyridine-3-carboxylate

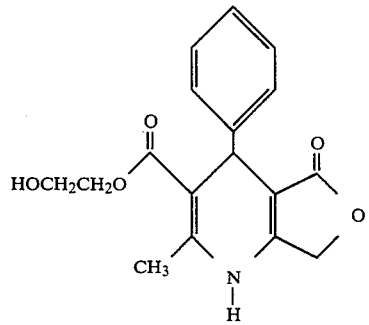

2.33 grams of 80 percent pyridinium bromide perbromide (1.46 millimoles) was added to a solution of 500 milligrams (1.51 millimoles) of bis(2-hydroxyethyl) 2,6-dimethyl-4-phenyl-1,4-dihydropyridine-3,5-dicarboxylate in 400 milliliters of ethylene dichloride and 1.6 milliliters of pyridine. The resulting mixture was stirred at 0° C. for 1 hour and then heated at reflux temperature for 2 hours. Thereafter, the mixture was cooled to room temperature, the resulting solution washed with 2N hydrochloric acid, sodium bicarbonate solution and brine, dried over magnesium sulfate, filtered, and the filtrate subjected to reduced pressure to vaporize the solvent and to recover as residue a semi-crystalline solid. The solid was not crystallizable from acetonitrile. The acetonitrile was vaporized to obtain an orange oil which on trituration with ethyl acetate produced crystals. The crystals, after recrystallization twice from ethyl acetate, had a melting point of 185°–186° C. $^1$H NMR and elemental analyses showed the product to have ethyl acetate solvate of crystallization. Elemental analyses were as follows:

Calc'd for $C_{18}H_{19}NO_5 \cdot 1/4 CH_3COOC_2H_5$: C, 64.99; H, 6.24; N, 3.87. found: C, 64.96; H, 6.10; N, 4.92.

EXAMPLE XV

3-Dimethylaminopropyl 2-methyl-4-phenyl-5-oxo-1,4,5,7-tetrahydrofuro[3,4-b]pyridine-3-carboxylate

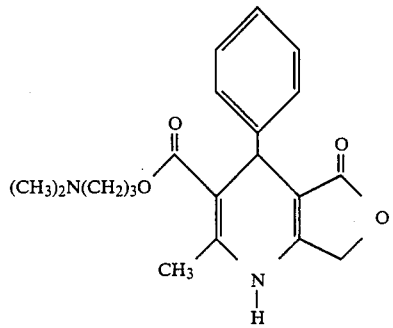

1.31 grams of 80 percent pyridinium bromide perbromide (3.28 millimoles) was added to a cooled to −20° C. solution of 1.30 grams (2.84 millimoles) of bis(3-dimethylaminopropyl) 2,6-dimethyl-4-phenyl-1,4-dihydropyridine-3,5-dicarboxylate and 0.4 milliliter of pyridine in 20 milliliters of chloroform. The resulting mixture was stirred at −20° C. for ½ hour and then heated at reflux for 2 hours. The mixture was cooled to room temperature and allowed to stir overnight. The crude product was chromatographed on silica gel with 1 percent methanol in chloroform saturated with ammonia as eluant to obtain 161 milligrams of an oil which crystallized when mixed with CDCl3 for NMR analysis. The product was concentrated in vacuo and recrystallized from ethyl acetate-hexane to obtain crystals of m.p. 112°–115° C. after drying 70° C. overnight. The product was a hydrate having elemental analyses as follows:

Calc'd for $C_{21}H_{26}N_2O_4 \cdot 1H_2O$: C, 64.93; H, 7.27; N, 7.23. Found: C, 65.25; H, 7.38; N, 7.25.

EXAMPLE XVI

In operations carried out in a manner similar to that above described, the following compounds may be prepared:

Isopropyl 2-methyl-4-(2-methoxyphenyl)-5-oxo-1,4,5,7-tetrahydrofuro[3,4-b]pyridine-3-carboxylate from diisopropyl 2,6-dimethyl-4-(2-methoxyphenyl)-1,4-dihydropyridine-3,5-dicarboxylate.

n-Hexyl 2-methyl-4-phenyl-5-oxo-1,4,5,7-tetrahydrofuro[3,4-b]pyridine-3-carboxylate from di(n-hexyl) 2,6-dimethyl-4-phenyl-1,4-dihydropyridine-3,5-dicarboxylate.

Phenyl 2-methyl-4-phenyl-5-oxo-1,4,5,7-tetrahydrofuro[3,4-b]pyridine-3-carboxylate from diphenyl 2,6-dimethyl-4-phenyl-1,4-dihydropyridine-3,5-dicarboxylate.

Benzyl 2-methyl-4-(2-chlorophenyl)-5-oxo-1,4,5,7-tetrahydrofuro[3,4-b]pyridine-3-carboxylate from dibenzyl 2,6-dimethyl-4-phenyl-1,4-dihydropyridine-3,5-dicarboxylate.

2-Chloroethyl 2-methyl-4-phenyl-5-oxo-1,4,5,7-tetrahydrofuro[3,4-b]pyridine-3-carboxylate from bis(2-chloroethyl) 2,6-dimethyl-4-phenyl-1,4-dihydropyridine-3,5-dicarboxylate.

2-Methoxyethyl 2-methyl-4-phenyl-5-oxo-1,4,5,7-tetrahydrofuro[3,4-b]pyridine-3-carboxylate from bis(2-methoxyethyl) 2,6-dimethyl-4-phenyl-1,4-dihydropyridine-3,5-dicarboxylate.

o-Tolyl 2-methyl-4-(4-halophenyl)-5-oxo-1,4,5,7-tetrahydrofuro[3,4-b]pyridine-3-carboxylate from di(o-tolyl) 2,6-dimethyl-4-(4-halophenyl)-1,4-dihydropyridine-3,5-dicarboxylate.

2-Phenylethyl 2-methyl-4-phenyl-5-oxo-1,4,5,7-tetrahydrofuro[3,4-b]pyridine-3-carboxylate from bis(2-phenylethyl) 2,6-dimethyl-4-phenyl-1,4-dihydropyridine-3,5-dicarboxylate.

4-Nitrophenyl 2-methyl-4-phenyl-5-oxo-1,4,5,7-tetrahydrofuro[3,4-b]pyridine-3-carboxylate from bis(4-nitrophenyl) 2,6-dimethyl-4-phenyl-1,4-dihydropyridine-3,5-dicarboxylate.

2-Nitroethyl 2-methyl-4-phenyl-5-oxo-1,4,5,7-tetrahydrofuro[3,4-b]pyridine-3-carboxylate from bis(2-nitroethyl) 2,6-dimethyl-4-phenyl-1,4-dihydropyridine-3,5-dicarboxylate.

PREPARATION OF STARTING MATERIAL

The 1,4-dihydropyridine diester starting materials of Formula II or IIA which are not available commercially may be prepared by heating together substantially equimolar proportions of the appropriate aromatic aldehyde, acetoacetic ester and alkyl β-aminocrotonate in a polar solvent such as ethanol for time sufficient to complete the reaction with the formation of the diester product and water by-product which is codistilled with ethanol. The product then may be recovered and purified employing conventional procedures.

What is claimed:

1. A process for preparing a tetrahydrofuro[3,4-b]pyridine compound having the formula

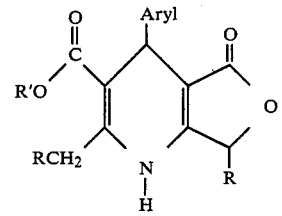

wherein R is hydrogen or methyl and R' is a residue of a hydroxy compound capable of forming esters with a carboxyl group, comprising reacting a 1,4-dihydropyridine diester compound having the formula

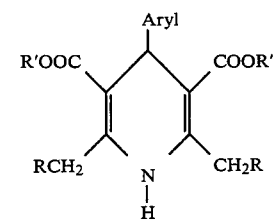

wherein R and R' are as above defined with a bromine generating agent in a dry inert dispersion medium.

2. A process for preparing alkyl 2-alkyl-4-aryl-5-oxo-1,4,5,7-tetrahydrofuro[3,4-b]pyridine-3-carboxylate compounds having the formula

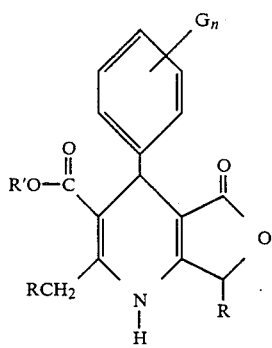

wherein

R is hydrogen or methyl

R' is alkyl, hydroxyalkyl, alkoxyalkyl, haloalkyl, aralkyl, cyanoalkyl, nitroalkyl, phenyl, alkylphenyl, alkoxyphenyl, halophenyl and nitrophenyl;

G is alkyl, alkoxy, halo, acyl, alkoxyalkyl, alkylenedioxy, alkylaminoalkyl, nitro, aryl, cyano, trifluoromethyl, haloalkyloxy, aralkyloxy, aryloxy, carbalkoxy, alkylsulfonyl, arylsulfonyl, alkylsulfinyl and arylsulfinyl, and n is from 0 to 5, which comprises intimately contacting a 4-aryl-1,4-dihydropyridine dicarboxylate compound having the formula

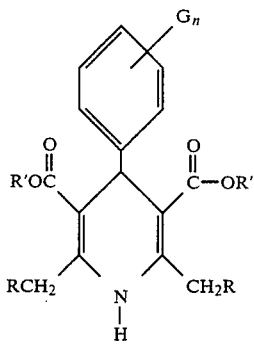

wherein R, R' G and n are as above defined with a bromine generating agent in an inert dispersion medium.

3. A process according to claim 1 wherein the bromine generating agent is pyridinium bromide perbromide.

4. A process according to claim 1 wherein the bromine generating agent is N-bromosuccinimide.

5. A process according to claim 3 wherein the pyridinium bromide perbromide is added in one portion to a solution of a 4-aryl-1,4-dihydropyridine dicarboxylate compound in an inert dispersion medium maintained in a dry, inert atmosphere at a temperature in the range of from about $-5°$ to $+5°$ C., thereafter heating the mixture to a temperature in the range of from about 40° to 100° C. for time sufficient to complete the reaction.

6. A process according to claim 3 wherein the dispersion medium is a halogenated hydrocarbon solvent and the reaction is completed by heating at the reflux temperature of the solvent.

* * * * *